United States Patent
Schweich, Jr. et al.

(10) Patent No.: US 6,629,921 B1
(45) Date of Patent: *Oct. 7, 2003

(54) HEART WALL TENSION REDUCTION APPARATUS AND METHOD

(75) Inventors: Cyril J. Schweich, Jr., St. Paul, MN (US); Todd J. Mortier, Minneapolis, MN (US); Robert M. Vidlund, Maplewood, MN (US); Peter T. Keith, St. Paul, MN (US); Thomas M. Paulson, Minneapolis, MN (US)

(73) Assignee: Myocor, Inc., St. Paul, MN (US)

(*) Notice: Subject to any disclaimer, the term of this patent is extended or adjusted under 35 U.S.C. 154(b) by 17 days.

This patent is subject to a terminal disclaimer.

(21) Appl. No.: 09/697,711

(22) Filed: Oct. 27, 2000

Related U.S. Application Data

(63) Continuation of application No. 09/497,118, filed on Feb. 3, 2000, which is a continuation-in-part of application No. 08/933,456, filed on Sep. 18, 1997, now Pat. No. 5,961,440, which is a continuation-in-part of application No. 08/778,277, filed on Jan. 2, 1997, now Pat. No. 6,050,936, which is a continuation of application No. 09/124,286, filed on Jul. 29, 1998, now Pat. No. 6,045,497.

(51) Int. Cl.[7] .......................... A61M 31/00; A61B 17/12
(52) U.S. Cl. ............................ 600/16; 600/37; 128/898
(58) Field of Search ............................ 600/16–18, 37; 601/11; 623/3.1, 14.13, 23.72, 904, 910, 922; 128/897, 898

(56) References Cited

U.S. PATENT DOCUMENTS

| | | | |
|---|---|---|---|
| 4,192,293 A | 3/1980 | Asrican | 600/18 |
| 4,261,342 A | 4/1981 | Aranguren Duo | 128/1 |
| 4,372,293 A | 2/1983 | Vijil-Rosales | 128/1 |
| 4,409,974 A | 10/1983 | Freedland | 128/92 |
| 4,536,893 A | 8/1985 | Parravicini | 623/3 |
| 4,690,134 A | 9/1987 | Snyders | 128/64 |
| 4,936,857 A | 6/1990 | Kulik | 623/3 |
| 4,944,753 A | 7/1990 | Burgess et al. | 623/16 |
| 4,960,424 A | 10/1990 | Grooters | 623/2 |
| 4,997,431 A | 3/1991 | Isner et al. | 606/15 |

(List continued on next page.)

FOREIGN PATENT DOCUMENTS

| | | |
|---|---|---|
| DE | 36 14 292 | 11/1987 |
| DE | 42 34 127 | 5/1994 |
| DE | 296 19 294 | 8/1997 |
| EP | 0 583 012 | 2/1994 |
| FR | 2 768 324 | 3/1999 |
| WO | 91/19465 | 12/1991 |
| WO | 95/06447 | 3/1995 |
| WO | 95/16476 | 6/1995 |
| WO | 96/04852 | 2/1996 |
| WO | 96/40356 | 12/1996 |

(List continued on next page.)

OTHER PUBLICATIONS

Edie, M.D. et al., "Surgical repair of single ventricle," *The Journal of Thoracic and Cardiovascular Surgery*, vol. 66, No. 3, Sep., 1973, pp. 350–360.

McGoon, M.D. et al., "Correction of the univentricular heart having two atrioventricular valves," *The Journal of Thoracic and Cardiovascular Surgery*, vol. 74, No. 2, Aug., 1977, pp. 218–226.

(List continued on next page.)

*Primary Examiner*—Jeffrey R. Jastrzab
(74) *Attorney, Agent, or Firm*—Finnegan, Henderson, Farabow, Garrett & Dunner, LLP

(57) ABSTRACT

An apparatus for treatment of a failing heart by reducing the wall tension therein. In one embodiment, the apparatus includes a tension member for drawing at least two walls of a heart chamber toward each other. Methods for placing the apparatus on the heart are also provided.

22 Claims, 14 Drawing Sheets

U.S. PATENT DOCUMENTS

| | | | |
|---|---|---|---|
| 5,106,386 A | 4/1992 | Isner et al. | 606/15 |
| 5,131,905 A | 7/1992 | Grooters | 600/16 |
| RE34,021 E | 8/1992 | Mueller et al. | 604/51 |
| 5,169,381 A | 12/1992 | Snyders | 600/16 |
| 5,192,314 A | 3/1993 | Daskalakis | 623/3 |
| 5,250,049 A | 10/1993 | Michael | 606/72 |
| 5,284,488 A | 2/1994 | Sideris | 606/213 |
| 5,385,528 A | 1/1995 | Wilk | 600/18 |
| 5,433,727 A | 7/1995 | Sideris | 606/213 |
| 5,450,860 A | 9/1995 | O'Connor | 128/898 |
| 5,452,733 A | 9/1995 | Sterman et al. | 128/898 |
| 5,458,574 A | 10/1995 | Machold et al. | 604/101 |
| 5,496,305 A | 3/1996 | Kittrell et al. | 606/15 |
| 5,509,428 A | 4/1996 | Dunlop | 128/898 |
| 5,533,958 A | 7/1996 | Wilk | 600/18 |
| 5,571,215 A | 11/1996 | Sterman et al. | 623/66 |
| 5,584,803 A | 12/1996 | Stevens et al. | 604/4 |
| 5,593,424 A | 1/1997 | Northrup, III | 606/232 |
| 5,682,906 A | 11/1997 | Sterman et al. | 128/898 |
| 5,702,343 A | 12/1997 | Alferness | 607/37 |
| 5,718,725 A | 2/1998 | Sterman et al. | 623/2 |
| 5,800,334 A | 9/1998 | Wilk | 600/18 |
| 5,800,528 A | 9/1998 | Lederman et al. | 623/3 |
| 5,814,097 A | 9/1998 | Sterman et al. | 623/2 |
| 5,849,005 A | 12/1998 | Garrison et al. | 606/1 |
| 5,855,614 A | 1/1999 | Stevens et al. | 623/11 |
| 5,865,791 A | 2/1999 | Whayne et al. | 604/49 |
| 5,902,229 A | 5/1999 | Tsitlik et al. | 600/46 |
| 5,957,977 A | 9/1999 | Melvin | 623/3 |
| 5,961,440 A | 10/1999 | Schweich, Jr. et al. | |
| 5,971,910 A | 10/1999 | Tsitlik et al. | 600/16 |
| 5,984,857 A | 11/1999 | Buck et al. | 606/16 |
| 6,024,096 A | 2/2000 | Buckberg | |
| 6,024,756 A | 2/2000 | Huebsch et al. | 606/213 |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A | 6/2000 | Laufer | 607/96 |
| 6,077,214 A | 6/2000 | Mortier et al. | 600/16 |
| 6,077,218 A | 6/2000 | Alferness | 600/37 |
| 6,079,414 A | 6/2000 | Roth | 128/898 |
| 6,085,754 A | 7/2000 | Alferness et al. | 128/898 |
| 6,095,968 A | 8/2000 | Snyders | 600/16 |
| 6,110,100 A | 8/2000 | Talpade | 600/37 |
| 6,117,159 A | 9/2000 | Huebsch et al. | 606/213 |
| 6,123,662 A | 9/2000 | Alferness et al. | 600/37 |
| 6,125,852 A | 10/2000 | Stevens et al. | 128/898 |
| 6,126,590 A | 10/2000 | Alferness | 600/37 |
| 6,155,968 A | 12/2000 | Wilk | 600/16 |
| 6,155,972 A | 12/2000 | Nauertz et al. | 600/37 |
| 6,162,168 A | 12/2000 | Schweich, Jr. et al. | 600/16 |
| 6,165,119 A | 12/2000 | Schweich, Jr. et al. | 600/16 |
| 6,165,120 A | 12/2000 | Schweich, Jr. et al. | 600/16 |
| 6,165,121 A | 12/2000 | Alferness | 600/37 |
| 6,165,122 A | 12/2000 | Alferness | 600/37 |
| 6,169,922 B1 | 1/2001 | Alferness et al. | 607/5 |
| 6,174,279 B1 | 1/2001 | Girard | 600/37 |
| 6,179,791 B1 | 1/2001 | Krueger | 600/587 |
| 6,190,408 B1 | 2/2001 | Melvin | 623/3.1 |

FOREIGN PATENT DOCUMENTS

| | | |
|---|---|---|
| WO | 97/24101 | 7/1997 |
| WO | 98/03213 | 1/1998 |
| WO | 98/14136 | 4/1998 |
| WO | 98/18393 | 5/1998 |
| WO | 98/26738 | 6/1998 |
| WO | 98/29041 | 7/1998 |
| WO | 98/32382 | 7/1998 |
| WO | 99/11201 | 3/1999 |
| WO | 99/13777 | 3/1999 |
| WO | 99/30647 | 6/1999 |
| WO | 99/44534 | 9/1999 |
| WO | 99/44680 | 9/1999 |
| WO | 99/52470 | 10/1999 |
| WO | 99/56655 | 11/1999 |
| WO | 00/02500 | 1/2000 |
| WO | 00/13722 | 3/2000 |
| WO | 00/18320 | 4/2000 |
| WO | 00/28912 | 5/2000 |
| WO | 00/28918 | 5/2000 |
| WO | 00/36995 | 6/2000 |
| WO | 00/42919 | 7/2000 |
| WO | 00/45735 | 8/2000 |
| WO | 00/62727 | 10/2000 |
| WO | 01/03608 | 1/2001 |

OTHER PUBLICATIONS

Lev, M.D., et al., "Single (Primitive) Ventricle," *Circulation*, vol. 39, May, 1969, pp. 577–591.

Westaby with Bosher, "Landmarks in Cardiac Surgery," 1997, pp. 198–199.

Shumacker, "Cardiac Aneurysms," *The Evolution of Cardiac Surgery*, 1992, pp. 159–165.

Feldt, M.D., "Current status of the septation procedure for univentricular heart," *The Journal of Thoracic and Cardiovascular Surgery*, vol. 82, No. 1, Jul., 1981, pp. 93–97.

Doty, M.D., "Septation of the univentricular heart," *The Journal of Thoracic and Cardiovascular Surgery*, vol. 78, No. 3, Sep., 1979, pp. 423–430.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," *J. Card. Surg.*, 1996:11:99–108.

Ianuzzo et al., "On Preconditioning of Skeletal Muscle: Application to Dynamic Cardiomyoplasty," Invited Commentary, *J. Card. Surg.*, 1996:11:109–110.

Chachques et al., "Latissimus Dorsi Dynamic Cardiomyoplasty," *Ann. Thorac. Surg.*, 1989:47:600–604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long–Term Follow–Up (12 to 35 Weeks) After Dynamic Cardiomyoplasty," *JACC*, vol. 22, No. 3, Sep. 1993:758–67.

Batista et al., "Partial Left Ventriculectomy to Improve Left Ventricular Function in End–Stage Heart Disease," *J. Card. Surg.*, 1996:11:96–98.

"Congestive Heart Failure in the United States: A New Epidemic" Data Fact Sheet, National Heart, Lung, and Blood Institute, National Institutes of Health, Dec. 9, 1996, pp. 1–6.

Kormos et al., "Experience with Univentricular Support in Mortally Ill Cardiac Transplant Candidates," *Ann. Thorac. Surg.*, 1990:49:261–71.

Wampler et al., "Treatment of Cardiogenic Shock with the Hemopump Left Ventricular Assist Device," *Ann. Thorac. Surg.*, 1991:52:506–13.

McCarthy et al., "Clinical Experience with the Novacor Ventricular Assist System," *J. Thorac. Cardiovasc. Surg.*, 1991:102–578–87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to January 2, 1997, pp. 626–628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629–631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632–636.

Bearnson et al., "Development of a Prototype Magnetically Suspended Rotor Ventricular Assist Device," ASAIO Journal, 1996, pp. 275–280.

Sakakibara et al., "A Muscle Powered Cardiac Assist Device for Right Ventricular Support: Total Assist of Partial Assist?," Trans. Am.Soc. Artif. Intern. Organs, vol. XXXVI, 1990, pp. 372–375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, ABIOMED's Temporary Artificial Heart System Reaches 200 U.S. Medical Center Milestone, 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED Wins NIH Grant to Develop Calcification–Resistant Plastic Heart Valve," 1 page.

Press Release dated Aug. 25, 1995, "ABIOMED Wins Research Grant from NIH to Develop Suturing Instrument for Abdominal surgery," 1 page.

Press Release dated Aug. 11, 1995, "ABIOMED Receives Grant from NIH Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS–5000 in More Than 100 U.S. Medical Centers," 1 page.

"Reversible Cardiomyopathy," Thoratec's Heartbeat, vol. 10.2, Aug. 1996, 4 pages.

Tsai et al., "Surface Modifying Additives for Improved Device–Blood Compatibility," ASAIO Journal, 1994, pp. 619–624.

Farrar et al., "A New Skeletal Muscle Linear–Pull Energy Convertor as a Power Source for Prosthetic Support Devices," The Journal of Heart & Lung Transplantation, vol. 11, No. 5, Sep., 1992, pp. 341–349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac–Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilaged Cardiomypathy—Short Term Results," date even with or prior to Jan. 2, 1997, 1 page.

Bach et al., "Early Improvement in Congestive Heart Failure after Correction of Secondary Mitral Regurgitation in End–Stage Cardiomyopathy," American Heart Journal, Jun. 1995, pp. 1165–1170.

Schuler et al., "Temporal Response of Left Ventricular Performance to Mitral Valve Surgery," vol. 59, No. 6, Jun. 1979, pp. 1218–1231.

Huikuri, "Effect of Mitral Valve Replacement on Left Ventricular Function in Mitral Regurgitation," Br. Heart J., vol. 49, 1983, pp. 328–333.

Pitarys II et al., "Long–Term Effects of Excision of the Mitral Apparatus on Global and Regional Ventricular Function in Humans," JACC, vol. 15, No. 3, Mar. 1, 1990, pp. 557–563.

Bolling et al., "Surgery for Acquired Heart Disease/Early Outcome of Mitral Valve Reconstruction in Patients with End–Stage Cardiomyopathy," The Journal of Thoracic and Cardiovascular Surgery, vol. 109, No. 4, Apr. 1995, pp. 676–683.

Masahiro et al., "Surgery for Acquired Heart Disease/Effects of Preserving Mitral Apparatus on Ventricular Systolic Function in Mitral Valve Operations in Dogs," The Journal of Thoracic and Cardiovascular Surgery, vol. 106, No. 6, Dec. 1993, pp. 1138–1146.

Dickstein et al., "Heart Reduction Surgery: An Analysis of the Impact on Cardiac Function," The Journal of Thoracic and Cardiovascular Surgery, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the $77^{th}$ Annual Meeting of the American Association of Thoracic Surgeons, May 1997, 33 pages.

Alonso–Lej, M.D., "Adjustable Annuloplasty for Tricuspid Insufficiency," The Annals of Thoracic Surgery, vol. 46, No. 3, Sep. 1988, 2 pages.

Kurlansky et al., "Adjustable Annuloplasty for Tricuspid Insufficiency," Ann. Thorac. Surg., 44:404–406, Oct. 1987.

Savage, M.D., "Repair of left ventricular aneurysm," The Journal of Thoracic and Cardiovascular Surgery, vol. 104, No. 3, Sep. 3, 1992, pp. 752–762.

Melvin, "Ventricular Radius Reduction Without Restriction: A Computational Analysis," ASAIO Journal, 45:160–165, 1999.

Cox, "Left Ventricular Aneurysms: Pathophysiologic Observations and Standard Resection," Seminars in Thoracic and Cardiovascular Surgery, vol. 9, No. 2, Apr., 1997, pp. 113–122.

Boyd et al., "Tricuspid Annuloplasty," The Journal of Thoracic Cardiovascular Surgery, vol. 68, No. 3, Sep. 1974, 8 pages.

"Heart 'jacket' could help stop heart failure progression," Clinica, 916, Jul. 10, 2000.

McCarthy et al., "Device Based Left Ventricular Shape Change Immediately Reduces Left Ventricular Volume and Increases Ejction Fraction in a Pacing Induced Cardiomyopathy Model in Dogs: A Pilot Study," *JACC*, Feb. 2000.

Acorn Cardiovascular, Inc. Abstracts, Nov. 13, 2000.

Acorn Cardiovascular Summary, undated, 1 page.

"Nations's First 'Heart Jacket' Surgery to Treat Heart Failure Performed at HUP; Novel 'Cardiac Support Device' Comes to America After Promising Results in Europe," Jun. 26, 2000, 3 pages.

Acorn Cardiovascular Company Overview, Jun. 2000, 6 pages.

Acorn Cardiovascular Company Overview, undated, 2 pages.

Acorn Cardiovascular Executive Summary, May 2000, 7 pages.

Acorn Cardiovascular Highlights, Abstracts, Mar. 10, 1999.

Acorn Cardiovascular Highlights, Abstracts, Apr. 19, 1999.

Acorn Cardiovascular Highlights, Abstracts, Oct. 1, 1999.

Acorn Cardiovascular Highlights, Abstracts, Nov. 9, 1999.

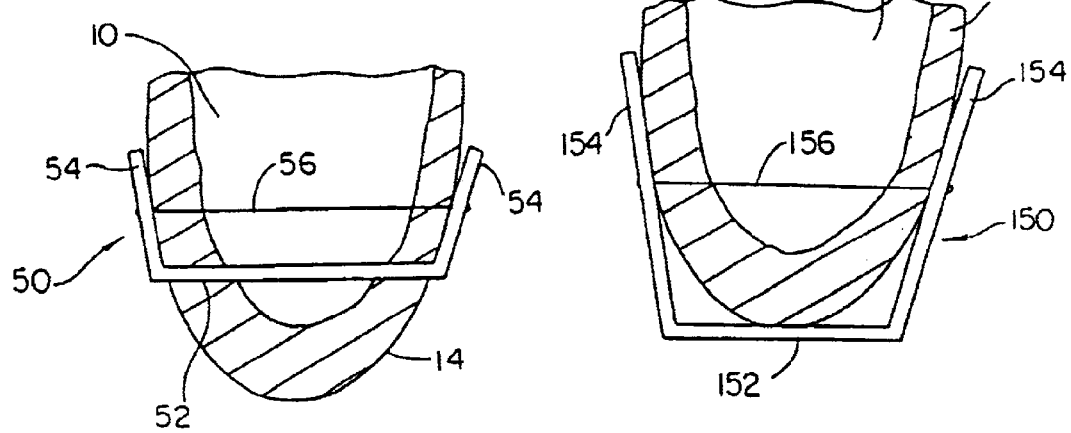
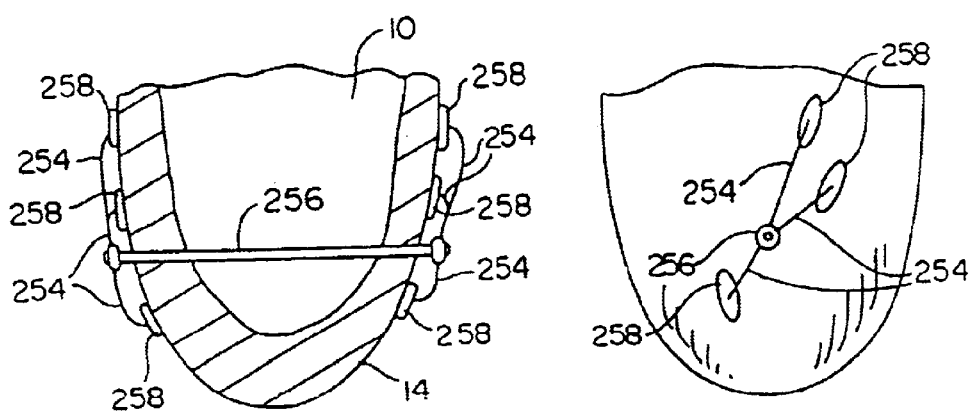

HEART WALL TENSION REDUCTION APPARATUS AND METHOD

CROSS REFERENCE TO RELATED APPLICATION

This application is a continuation of application Ser. No. 09/497,118, filed Feb. 3, 2000, which is a continuation of application Ser. No. 09/124,286, filed Jul. 29, 1998, now U.S. Pat. No. 6,045,497, which is a continuation-in-part of application Ser. No. 08/933,456, filed Sep. 18, 1997, now U.S. Pat. No. 5,961,440 which is a continuation-in-part of application Ser. No. 08/778,277, filed Jan. 2, 1997, now U.S. Pat. No. 6,050,936, all of which are hereby incorporated by reference herein.

FIELD OF THE INVENTION

The present invention pertains to the field of apparatus for treatment of a failing heart. In particular, the apparatus of the present invention is directed toward reducing the wall stress in the failing heart.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure. Typically resulting in dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into three generally categories. The first being pharmacological, for example, diuretics. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP); or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes like digoxin are cardiac glycosides and function to increase cardiac output by increasing the force and speed of cardiac muscle contraction. These drug therapies offer some beneficial effects but do not stop the progression of the disease.

Assist devices include mechanical pumps. Mechanical pumps reduce the load on the heart by performing all or part of the pumping function normally done by the heart. Currently, mechanical pumps are used to sustain the patient while a donor heart for transplantation becomes available for the patient.

There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention pertains to a non-pharmacological, passive apparatus and method for the treatment of a failing heart. The device is configured to reduce the tension in the heart wall. It is believed to reverse, stop or slow the disease process of a failing heart as it reduces the energy consumption of the failing heart, decreases isovolumetric contraction, increases isotonic contraction (sarcomere shortening), which in turn increases stroke volume. The device reduces wall tension during diastole and systole.

Those apparatus of the present invention which reduce heart wall stress by changing chamber wall geometry can be referred to as "splints". Splints can be grouped as either "full cycle splints" which engage the heart to produce a chamber shape change throughout the cardiac cycle, or "restrictive splints" which do not engage the heart wall at end systole to produce a chamber shape change.

In one embodiment, the apparatus includes a tension member for drawing at least two walls of the heart chamber toward each other to reduce the radius or area of the heart chamber in at least one cross sectional plane. The tension member has anchoring members disposed at opposite ends for engagement with the heart or chamber wall.

In another embodiment, the apparatus includes a compression member for drawing at least two walls of a heart chamber toward each other. In one embodiment, the compression member, includes a balloon. In another embodiment of the apparatus, a frame is provided for supporting the compression member.

Yet another embodiment of the invention includes a clamp having two ends biased toward one another for drawing at least two walls of a heart chamber toward each other. The clamp includes at least two ends having atraumatic anchoring member disposed thereon for engagement with the heart or chamber wall.

In yet another embodiment, a heart wall tension reduction apparatus is provided which includes a first tension member having two oppositely disposed ends and first and second elongate anchor members. A second tension member can be provided. One of the elongate anchors may be substituted for by two smaller anchors.

In an alternate embodiment of the heart wall tension reduction apparatus, an elongate compression member can be provided. First and second elongate lever members preferably extend from opposite ends of the compression member. A tension member extends between the first and second lever members.

The compression member of the above embodiment can be disposed exterior to, or internally of the heart. The tension member extends through the chamber or chambers to bias the lever members toward the heart.

In yet another embodiment of a heart wall tension reduction apparatus in accordance with the present invention, a rigid elongate frame member is provided. The frame member can extend through one or more chambers of the heart. One or more cantilever members can be disposed at opposite ends of the frame member. Each cantilever member includes at least one atraumatic pad disposed thereon. The atraumatic pads disposed at opposite ends of the frame member can be biased toward each other to compress the heart chamber.

One method of placing a heart wall tension apparatus or splint on a human heart includes the step of extending a hollow needle through at least one chamber of the heart such that each end of the needle is external to the chamber. A flexible leader is connected to a first end of a tension member. A second end of the tension member is connected to an atraumatic pad. The leader is advanced through the needle from one end of the needle to the other. The leader is further advanced until the second end of the tension member is proximate the heart and the first end of the tension member is external to the heart. A second atraumatic pad is connected to the first end of the tension member such that the first and second atraumatic pads engage the heart.

Yet another method of placing a heart wall tension apparatus on a heart includes the step of extending a needle having a flexible tension member releasably connected thereto through at least one chamber of the heart such that opposite ends of the tension member are external to the chamber and exposed on opposite sides of the chamber. The needle is removed from the tension member. Then first and second atraumatic pads are connected to the tension member at opposite ends of the tension member.

BRIEF DESCRIPTION OF THE DRAWINGS

FIG. 13 is a vertical cross-sectional view of a chamber of a human heart showing a compression member version of the splint in accordance with the present invention;

FIG. 14 is a vertical cross-sectional view of a chamber of a human heart showing another version of the splint shown in FIG. 13;

FIG. 15 is a vertical cross-sectional view of a chamber of a human heart showing a frame member version of the splint in accordance with the present invention;

FIG. 16 is an end view of the splint of FIG. 15;

DETAILED DESCRIPTION OF THE INVENTION

Figure 1:
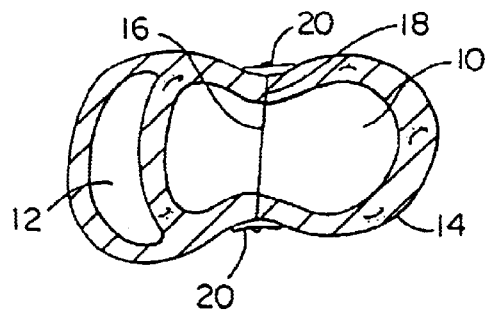
FIG. 1 is a transverse cross-section of the left and right ventricles of a human heart showing the placement of a splint in accordance with the present invention.

Referring now to the drawings wherein like reference numerals refer to like elements throughout the several views, FIG. 1 shows a transverse cross-section of a left ventricle 10 and a right ventricle 12 of a human heart 14. Extending through the left ventricle is a splint 16 including a tension member 18 and oppositely disposed anchors 20. Splint 16 as shown in FIG. 1 has been positioned to draw opposite walls of left ventricle 10 toward each other to reduce the "radius" of the left ventricular cross-section or the cross-sectional area thereof to reduce left ventricular wall stresses. It should be understood that although the splint 16 and the alternative devices disclosed herein are described in relation to the left ventricle of a human heart, these devices could also be used to reduce the radius or cross-sectional area of the other chambers of a human heart in transverse or vertical directions, or at an angle between the transverse and vertical.

Those apparatus of the present invention which reduce heart wall stress by changing chamber wall geometry can be referred to as "splints". "Full cycle splints" engage the heart to produce a chamber shape change throughout the cardiac cycle. "Restrictive splints" do not engage the heart wall at end systole to produce a chamber shape change.

Figure 2:
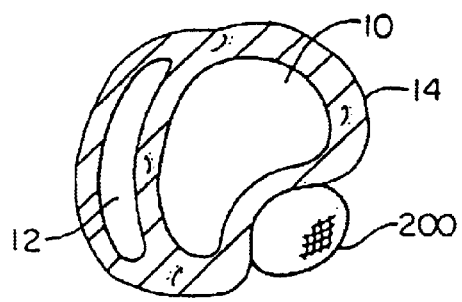
FIG. 2 is a transverse cross-section of the left and right ventricles of a human heart showing the placement of a balloon device in accordance with the present invention.

FIG. 2 discloses an alternate embodiment of the present invention, wherein a balloon 200 is deployed adjacent the left ventricle. The size and degree of inflation of the balloon can be varied to reduce the radius or cross-sectional area of left ventricle 10 of heart 14.

Figure 3:
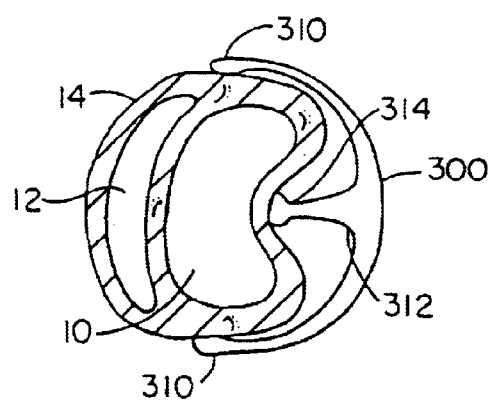
FIG. 3 is a transverse cross-section of the left and right ventricles of a human heart showing the placement of an external compression frame structure in accordance with the present invention.

FIG. 3 shows yet another alternative embodiment of the present invention deployed with respect to left ventricle 10 of human heart 14. Here a compression frame structure 300 is engaged with heart. 14 at atraurnatic anchor pads 310. A compression member 312 having an atraumatic surface 314 presses against a wall of left ventricle 10 to reduce the radius or cross-sectional area thereof.

Figure 4:
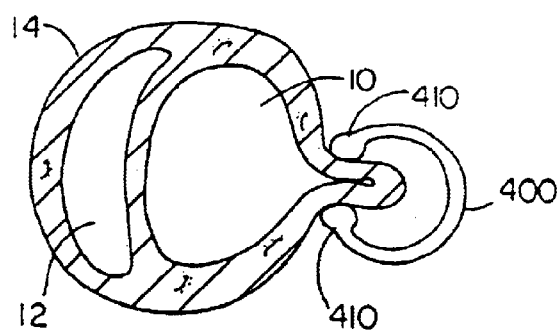
FIG. 4 is a transverse cross-section of the left and right ventricles of a human heart showing a clamp in accordance with the present invention.

FIG. 4 is a transverse cross-sectional view of human heart 14 showing yet another embodiment of the present invention. In this case a clamp 400 having atraumatic anchor pads 410 biased toward each other is shown disposed on a wall of left ventricle 10. Here the radius or cross-sectional area of left ventricle 10 is reduced by clamping off the portion of the wall between pads 410. Pads 410 can be biased toward each other and/or can be held together by a locking device.

Each of the various embodiments of the present invention disclosed in FIGS. 1–4 can be made from materials which can remain implanted in the human body indefinitely. Such biocompatible materials are well-known to those skilled in the art of clinical medical devices.

Figure 5:
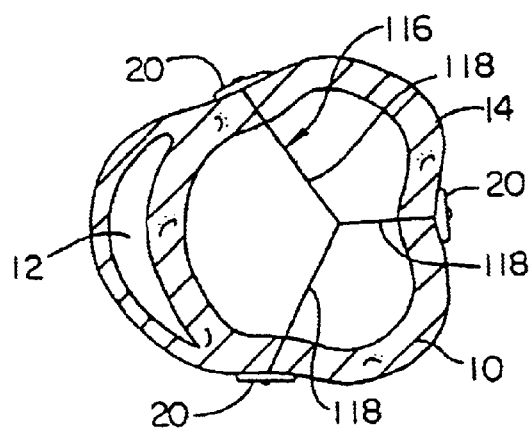
FIG. 5 is a transverse cross-section of the left and right ventricles of a human heart showing a three tension member version of the splint of FIG. 1.
Figure 6:
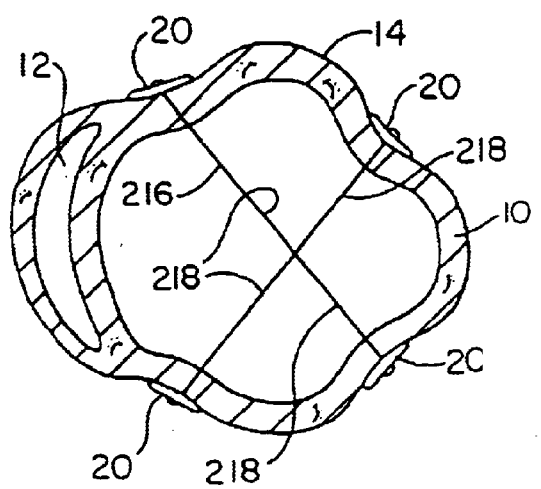
FIG. 6 is a transverse cross-section of the left and right ventricles of a human heart showing a two tension member version of the splint shown in FIG. 1.

FIG. 5 shows an alternate embodiment of the splint of FIG. 1 referred to in FIG. 5 by the numeral 116. The embodiment 116 shown in FIG. 5 includes three tension members 118 as opposed to a single tension member 18 as shown in FIG. 1. FIG. 6 shows yet another embodiment of the splint 216 having four tension members 218. It is anticipated that in some patients, the disease process of the failing heart may be so advanced that three, four or more tension members may be desirable to reduce the heart wall stresses more substantially than possible with a single tension member as shown in FIG. 1.

Figure 7:
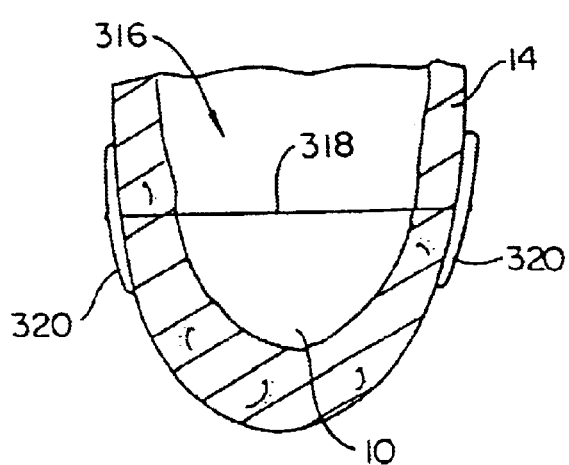
FIG. 7 is a vertical cross-sectional view of the left ventricle of a human heart showing an alternate version of the splint in accordance with the present invention.
Figure 8:
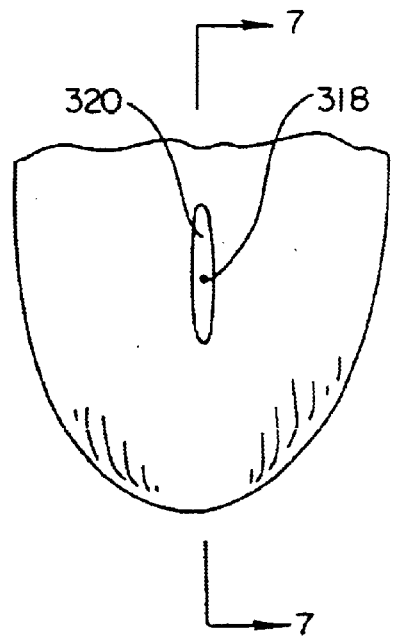
FIG. 8 is an end of the splint shown in FIG. 7.

FIG. 7 is a partial vertical cross-section of human heart 14 showing left ventricle 10. In FIG. 7, another splint embodiment 316 is shown having a tension member 318 extending through left ventricle 10. On opposite ends of tension member 318 are disposed elongate anchors or pads 320. FIG. 8 is an end view of tension member 318 showing elongate anchor 320.

Figure 9:
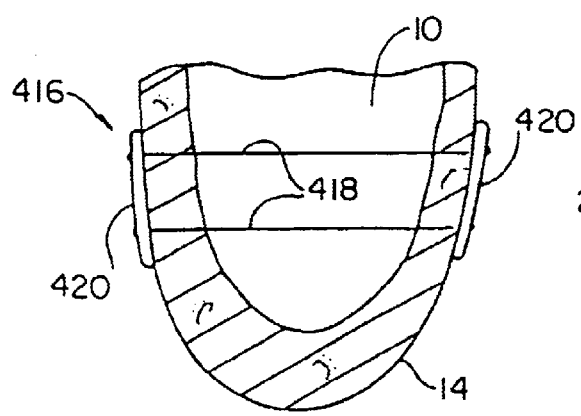
FIG. 9 is a vertical cross-sectional view of a chamber of a human heart showing another alternative embodiment of the splint in accordance with the present invention.

FIG. 9 shows another embodiment of a splint 416 disposed in a partial vertical cross-section of human heart 14. Splint 416 includes two elongate anchors or pads 420 similar to those shown in FIGS. 7 and 8. In FIG. 9, however, two tension members 418 extend through left ventricle 10 to interconnect anchors 420 on opposite sides of heart 14.

Figure 10:
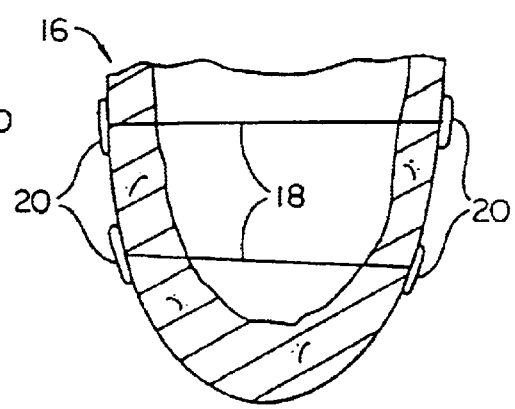
FIG. 10 is a vertical cross-section of a chamber of a human heart showing another alternative configuration of splints in accordance with the present invention.

FIG. 10 is a vertical cross section of heart 14 showing left ventricle 10. In this case, two splints 16 are disposed through left ventricle 10 and vertically spaced from each other to resemble the configuration of FIG. 9.

Figure 11:
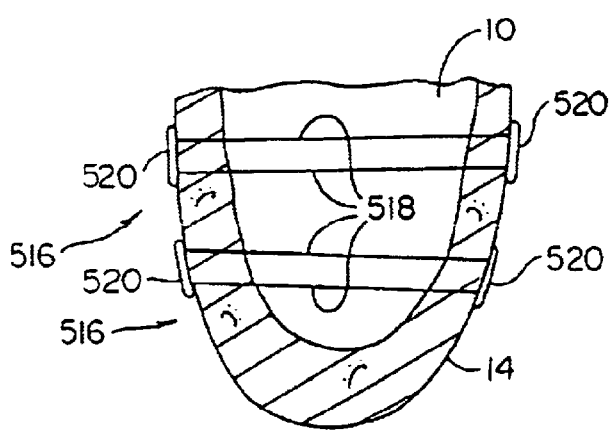
FIG. 11 is a vertical cross-sectional view of a chamber of a human heart showing another embodiment of a splint in accordance with the present invention.

FIG. 11 is a vertical cross sectional view of the left ventricle of heart 14. Two alternate embodiment splints 516 are shown extending through left ventricle 10. Each splint 516 includes two tension members 518 interconnecting two anchors or pads 520.

Figure 12:
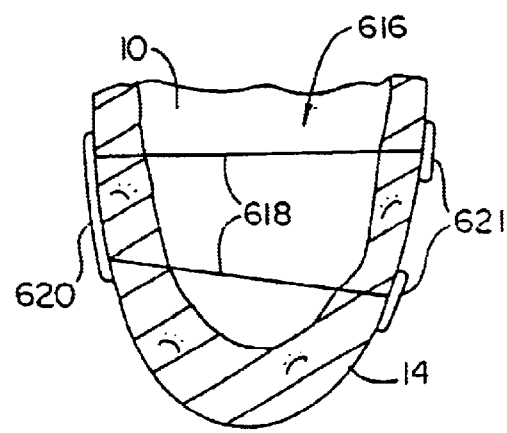
FIG. 12 is a vertical cross-sectional view of a chamber of a human heart showing another embodiment of the splint in accordance with the present invention.

FIG. 12 is yet another vertical cross sectional view of left ventricle 10 of heart 14. An alternate embodiment 616 of the splint is shown extending through left ventricle 10. Splint 616 includes an elongate anchor pad 620 and two shorter anchors or pads 621. Splint 616 includes two tension members 618. Each tension member 618 extends between anchors 620 and respective anchors 621.

FIG. 13 is a vertical cross sectional view of left ventricle 10 of heart 14. A splint 50 is shown disposed on heart 14. Splint 50 includes a compression member 52 shown extending through left ventricle 10. Opposite ends of compression member 52 are disposed exterior to left ventricle 10. Lever members 54 extend from each end of compression member 52 upwardly along the exterior surface of ventricle 10. A tension member 56 extends between lever members 54 to bias lever members 54 toward heart 14 to compress chamber 10. Compression member 52 should be substantially rigid, but lever members 54 and to some degree compression member 52 should be flexible enough to allow tension member 56 to bias lever members 54 toward heart 14.

Alternately, lever members 54 could be hinged to compression member 52 such that lever members 54 could pivot about the hinge when biased toward heart 14 by tension member 56.

FIG. 14 shows an alternate embodiment 156 of the splint shown in FIG. 13. In this case lever members 154 are longer than members 54 as compression member 152 of splint 150 has been disposed to the exterior of left ventricle 10.

FIG. 15 is a vertical cross sectional view of left ventricle 10 of heart 14. An alternate embodiment 250 of the splint is shown on heart 14. A preferably relatively rigid frame member 256 extends through ventricle 10. Disposed on opposite ends of frame 256 are cantilever member 254. Disposed on cantilever members 254 are atraumatic pads 258. Cantilever members 254 can be positioned along frame member 256 such that atraumatic pads 258 press against heart 14 to compress chamber 10. FIG. 16 is an end view of frame member 256 showing cantilever members 254 and pads 258.

It should be understood that each of the embodiments described above should be formed from suitable biocompatible materials known to those skilled in the art. The tension members can be formed from flexible or relatively more rigid material. The compression members and frame member should be formed from generally rigid material which may flex under load, but generally hold its shape.

Figure 17:
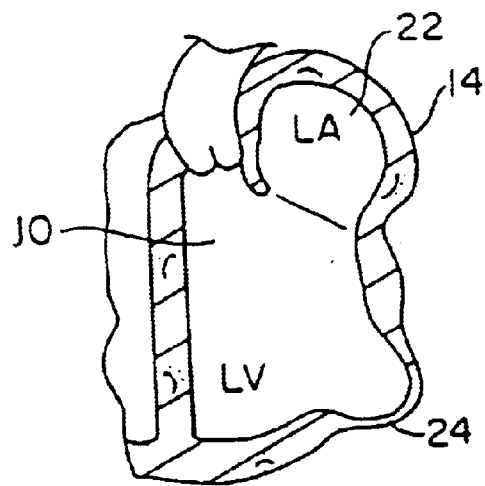
FIG. 17 is a vertical cross-section of the left ventricle and atrium, the left ventricle having scar tissue.

FIG. 17 is a partial vertical cross-section of human heart 14 showing left ventricle 10 and left atrium 22. As shown in FIG. 7, heart 14 includes a region of scar tissue 24 associated with an aneurysm or ischemia. As shown in FIG. 7, the scar tissue 24 increases the radius or cross-sectional area of left ventricle 10 in the region affected by the scar tissue. Such an increase in the radius or cross-sectional area of the left ventricle will result in greater wall stresses on the walls of the left ventricle.

Figure 18:
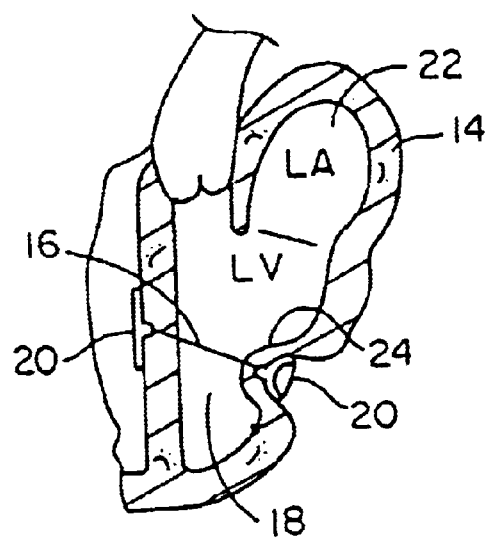
FIG. 18 is a vertical cross-section of the heart of FIG. 17 showing the splint of FIG. 1 drawing the scar tissue toward the opposite wall of the left ventricle.

FIG. 18 is a vertical cross-sectional view of the heart 14 as shown in FIG. 7, wherein a splint 16 has been placed to draw the scar tissue 24 toward an opposite wall of left ventricle 10. As a consequence of placing splint 16, the radius or cross-sectional area of the left ventricle affected by the scar tissue 24 is reduced. The reduction of his radius or cross-sectional area results in reduction in the wall stress in the left ventricular wall and thus improves heart pumping efficiency.

Figure 19:
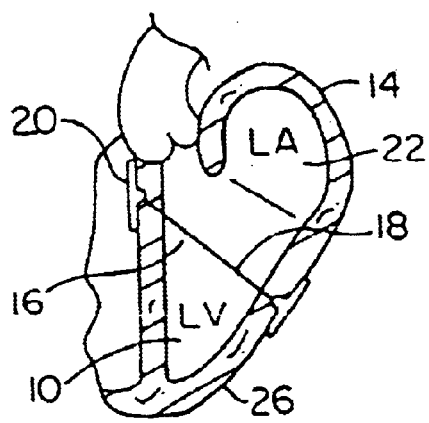
FIG. 19 is a vertical cross-section of the left ventricle and atrium of a human heart showing a version of the splint of FIG. 1 having an elongate anchor bar.

FIG. 19 is a vertical cross-sectional view of left ventricle 10 and left atrium 22 of heart 14 in which a splint 16 has been placed. As shown in FIG. 9, splint 16 includes an alternative anchor 26. The anchor 20 is preferably an elongate member having a length as shown in FIG. 9 substantially greater than its width (not shown). Anchor bar 26 might be used to reduce the radius or cross-sectional area of the left ventricle in an instance where there is generalized enlargement of left ventricle 10 such as in idiopathic dilated cardiomyopathy. In such an instance, bar anchor 26 can distribute forces more widely than anchor 20.

Figure 20:
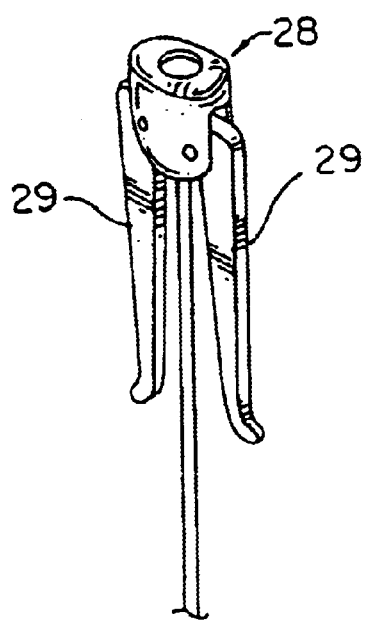
FIG. 20 is a side view of an undeployed hinged anchor member.
Figure 21:
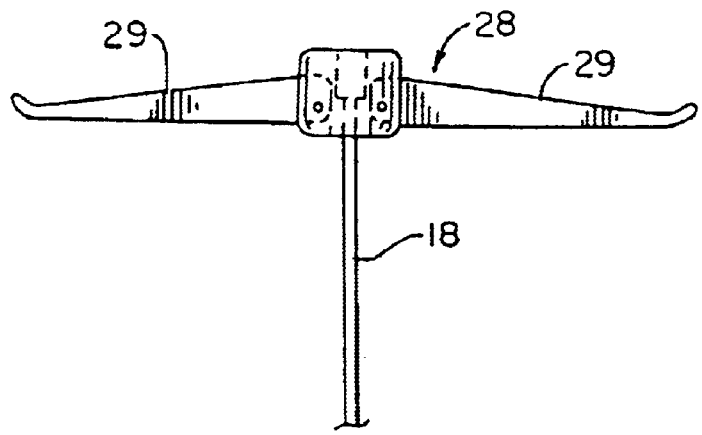
FIG. 21 is a side view of a deployed hinged anchor member of FIG. 10.

FIGS. 20 and 21 are side views of a hinged anchor 28 which could be substituted for anchors 20 in undeployed and deployed positions respectively. Anchor 28 as shown in FIG. 20 includes two legs similar to bar anchor 26. Hinged anchor 28 could include additional legs and the length of those legs could be varied to distribute the force over the surface of the heart wall. In addition there could be webbing between each of the legs to give anchor 28 an umbrella-like appearance. Preferably the webbing would be disposed on the surface of the legs which would be in contact with the heart wall.

Figure 22:
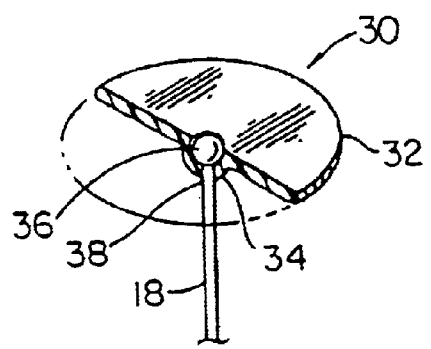
FIG. 22 is a cross-sectional view of an captured ball anchor member.

FIG. 22 is a cross-sectional view of a capture ball anchor 30. Capture ball anchor 30 can be used in place of anchor 20.

Capture ball anchor 30 includes a disk portion 32 to distribute the force of the anchor on the heart wall, and a recess 34 for receiving a ball 36 affixed to an end of tension member 18. Disk 32 and recess 34 include a side groove which allows tension member 38 to be passed from an outside edge of disk 32 into recess 34. Ball 36 can then be advanced into recess 34 by drawing tension member 18 through an opening 38 in recess 34 opposite disk 32.

Figure 23:
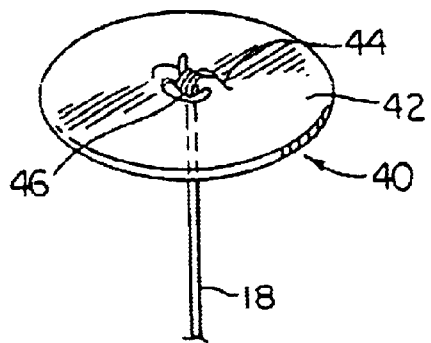
FIG. 23 is a perspective view of a cross bar anchor member.

FIG. 23 is a perspective view of a cross bar anchor 40. The cross bar anchor 40 can be used in place of anchors 20. The anchor 40 preferably includes a disk or pad portion 42 having a cross bar 44 extending over an opening 46 in pad 42. Tension member 18 can be extended through opening 46 and tied to cross bar 42 as shown.

Figure 24:
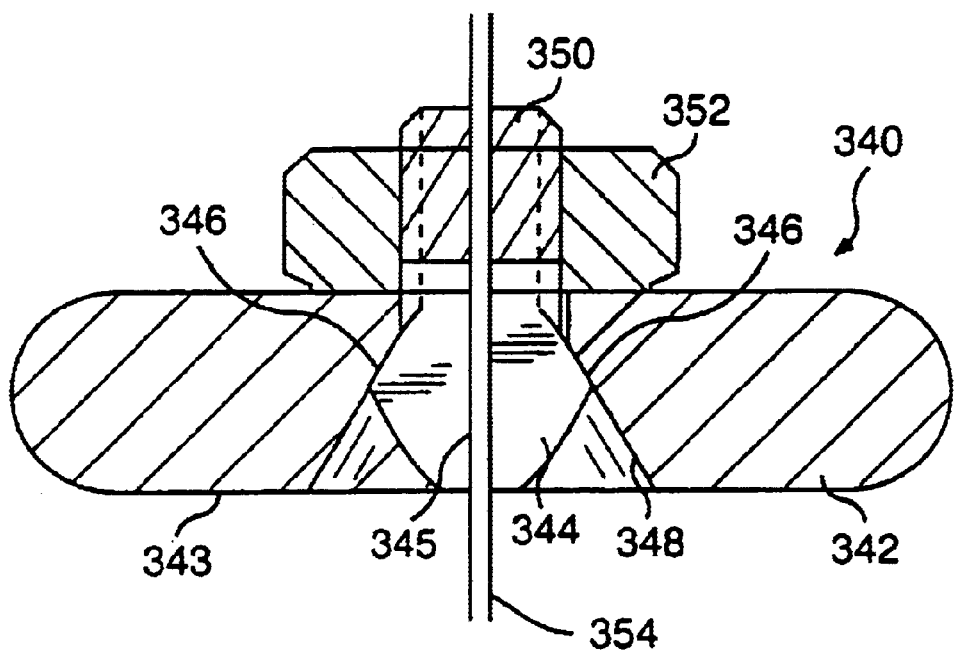
FIG. 24 is a cross sectional view of an alternate anchor pad.

FIG. 24 is a cross sectional view of an alternate embodiment of anchor pad 340 in accordance with the present invention. Anchor pad 340 preferably includes a disc shaped pad portion 342. Disc shape pad portion 342 includes side 343, which in use is disposed toward the heart. A conical aperture 348 having sloping sides 346 extends through pad 342. Collet 344 is disposed within orifice 348. A threaded portion 350 of collet 344 extends from orifice 348 opposite side 343, nut 352 is threaded over threaded portion 350. Lumen 345 extends through collet 344. A tension member 354 is shown extending through lumen 345. Lumen 345 has a diameter such that when nut 352 is not tightened on threaded portion 350, tension member 354 can slide freely through lumen 345. When nut 352 is tightened, it draws collet 344 away from side 343. Collet 344 is then pinched between walls 346 of orifice 348. When collet 344 is pinched, the size of lumen 345 is reduced such that tension member 354 can no longer move freely within lumen 345, fixing the position of pad 340 on tension member 354.

Figure 25:
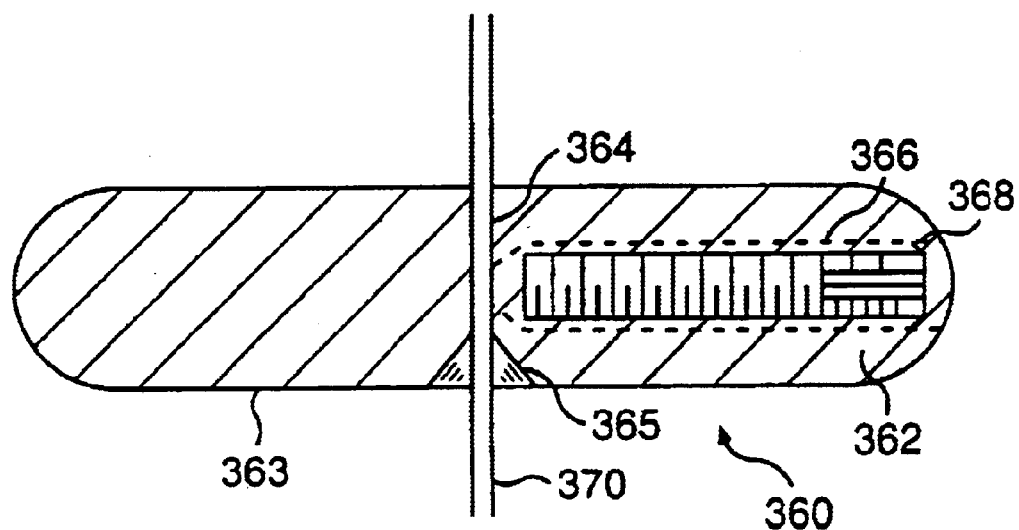
FIG. 25 is a cross sectional view of an alternate anchor pad.

FIG. 25 is a cross sectional view of an alternate embodiment an anchor pad 360 in accordance with the present invention. Anchor pad 360 includes a generally disc-shaped pad portion 362. Pad 362 includes a side 363 which when the pad is in use, is disposed toward the heart. A tension member lumen 364 extends through pad 362. Lumen 364 preferably has a generally conical shaped portion 365 disposed toward side 363. Tension member 370 is shown disposed through lumen 364 in FIG. 25. Pad 362 includes a threaded passage 366 extending from an edge of pad 362 to lumen 364. A set screw 368 is threaded into passage 366. Set screw 368 can be tightened to engage tension member 370 to fix the position of anchor pad 360. When set screw 368 is not tightened, the size of lumen 364 is preferably large enough that anchor pad 360 can slide relatively freely over tension member 370.

Figure 26:
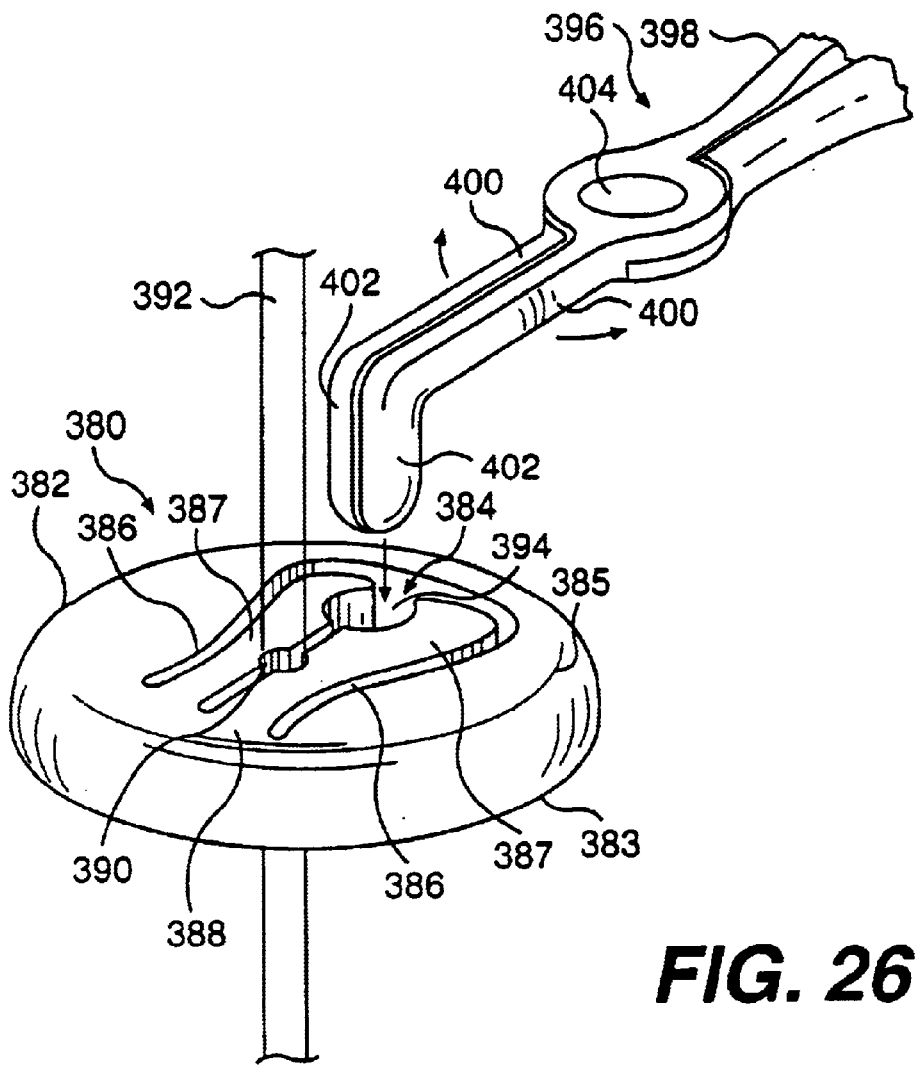
FIG. 26 is a perspective view of yet another alternate embodiment of an anchor pad including an anchor pad loosening device.

FIG. 26 is a perspective view of yet another embodiment of anchor pad 380 in accordance with the present invention. Anchor pad 380 preferably includes a generally disc-shaped pad portion 382 having a first side 383 which in use would be disposed toward the heart and a second side 385. Pad 382 as well as pads 342 and 362 are preferably formed from a metal such as stainless steel alloys or titanium alloys.

A tension member fastener 384 is formed in pad 382 by cutting a series of grooves and apertures through pad 382 from side 385 to side 383. A first groove 386 has a generally horseshoe shape. Second groove 388 extends between opposite portions of horseshoe shaped groove 386 to form two oppositely disposed cantilever members 387. A relatively large aperture 394 is formed between cantilever members 387 proximate their free ends. A second and smaller aperture 390 is formed closer to the fixed ends of cantilever members 387. Tension member 392 is shown extending through aperture 390.

As shown in FIG. 26, tension member 392 is clamped between cantilever members 387 such that the location of pad 382 is fixed along tension member 392. Pad 382 can be released by using a spreading device 396 to spread cantilever members 387 apart. Spreading device 396 includes handle 398 to spreading arms 400 each having a finger 402. Fingers 402 can be placed within aperture 394 then arms 400 and fingers 402 can be spread apart by pivoting them around a pin 404 such that cantilevers 387 are spread apart and pad 382 can move freely along tension member 392. It can be appreciated that although spreader 396 is shown extending transversely from tension member 392, it could also be configured such that fingers 402 do not curve transversely from arms 400 and thus spreader 396 could be disposed parallel to tension member 392. This would be particularly desirable in a situation where anchor pad 380 was being placed through a port or window during a less invasive splint implantation procedure. It can be appreciated that cantilever members 387 can be held apart such that pad 380 can be moved along tension member 392 by placement of a temporary wedge or pin in groove 388. For example, grooves 388 may include an additional small aperture disposed between aperture 390 and aperture 394 into which a pin could be placed to hold open members 387. When it is desired to fix the position of anchor pad 380 on tension member 392, device 396 could be used to spread. cantilever members 387 to remove the pin. The cantilever members could then be released to engage tension member 392. Aperture 390 of pad 380 can also include a conical portion disposed toward side 383 such as conical portion 365 of pad 360.

Cantilever arms 384 are preferably configured such that they do not stress tension member 392 beyond its elastic limit. It can also be appreciated that the force developed by cantilever members 387 impinging on tension member 392 is operator independent and defined by the geometry and material characteristics of members 387.

Figure 27:
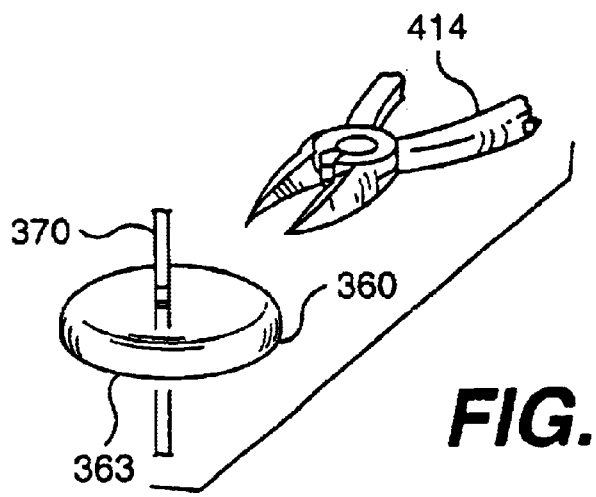
FIG. 27 is a perspective view of a tension member clip.

FIG. 27 is a perspective view of an anchor pad 360 having a tension member 370 extending therethrough. After pad 360 is secured to tension member 370, that portion of tension member 370 which extends from the side of anchor pad 360 opposite side 363 is preferably removed. This can be accomplished by trimming tension member 370 with wire cutter 414 or scissors. Although anchor pad 360 is used here to illustrate trimming tension member 370, it can be appreciated that in each of the embodiments disclosed herein there may be an excess portion of tension member extending from an anchor, which is preferably removed or trimmed.

Figure 28:
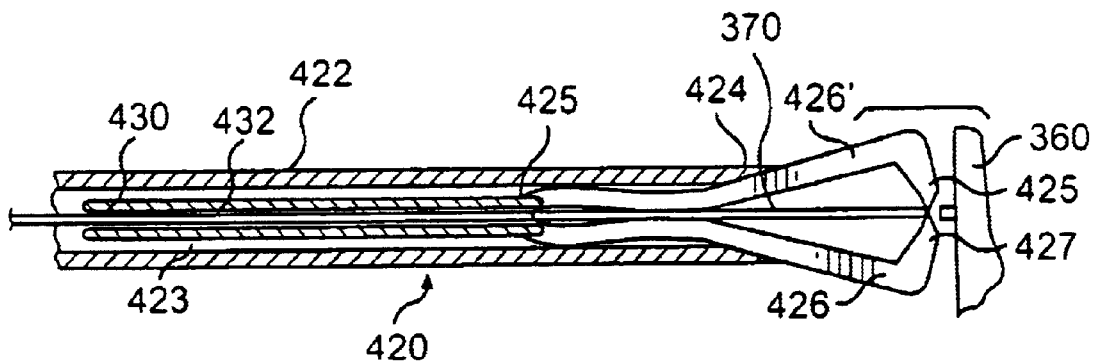
FIG. 28 is a cross sectional view of an alternate embodiment of a tension member clip.
Figure 29:
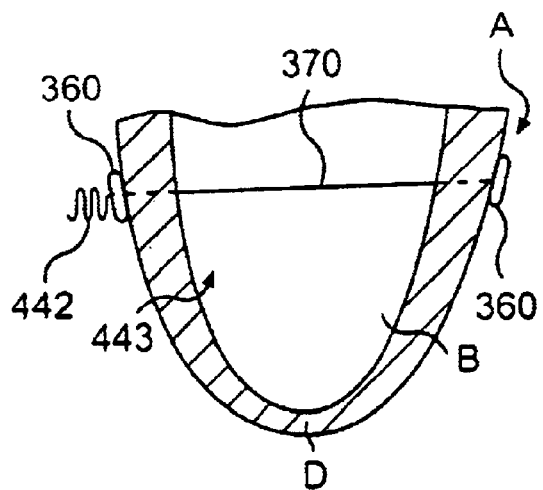
FIG. 29 is a cross sectional view of a heart including a tension member having a heat set end.

FIG. 28 is a cross sectional view of an alternate embodiment 420 of a tension member cutter. Device 420 includes an elongate outer tube 422 having a distal end 424. Tube 424 defines a lumen 423 through which extends a second tube 430 having a distal end 428. Extending distally from distal end 428 are two cutting arms 424 and 426 which are shown partially withdrawn into lumen 423 and transversely restrained by distal end 424 of outer tube 422. When unrestrained by distal end 424, arms 424 and 426 are biased apart. Each arm 424 and 426 has a cutting element 425 and 427, respectively. Elements 425 and 427 are shown in contact with each other in FIG. 28. A tension member 370 extends between arms 424 and through lumen 432 of inner tube 430. A representative anchor pad 360 is disposed adjacent elements 425 and 427. Device 420 of FIG. 28 is particularly useful when trimming excess tension member using less invasive techniques as it can be readily advanced over a tension member through a port or window trocar. FIG. 29 is a vertical cross sectional view of left ventricle B of heart A. A transventricular splint 443 including a tension member 370 and anchor pads 360 are shown disposed on heart A. To the left of heart A as shown in the figure is a coiled portion 442 of tension member 470. As an alternative to trimming an excess length of tension member, tension member 370 could be formed from a shape memory alloy such that portion 442 could be preset to assume a coil shape when warmed to near body temperature.

Once the length of the tension member has been adjusted, the anchors are secured in place along the tension member and the excess length of tension member removed if desired, the anchor or anchor pads are preferably secured in place on the heart. The anchor or anchor pads are secured such that relatively movement between the anchors or anchor pads and the heart is limited to reduce abrasion of the heart wall. To secure the anchor or anchor pads to heart A, a biocompatible adhesive could be placed between the pad and the heart to adhere the pad to the heart. Alternately, apertures could be provided in the pad such that sutures could be extended through the apertures and into the heart to secure the pad. In addition to sutures, the pad could include threaded apertures into which anchor screws could be advanced through the pad and into the heart wall to secure the pad to the heart.

Figure 30:
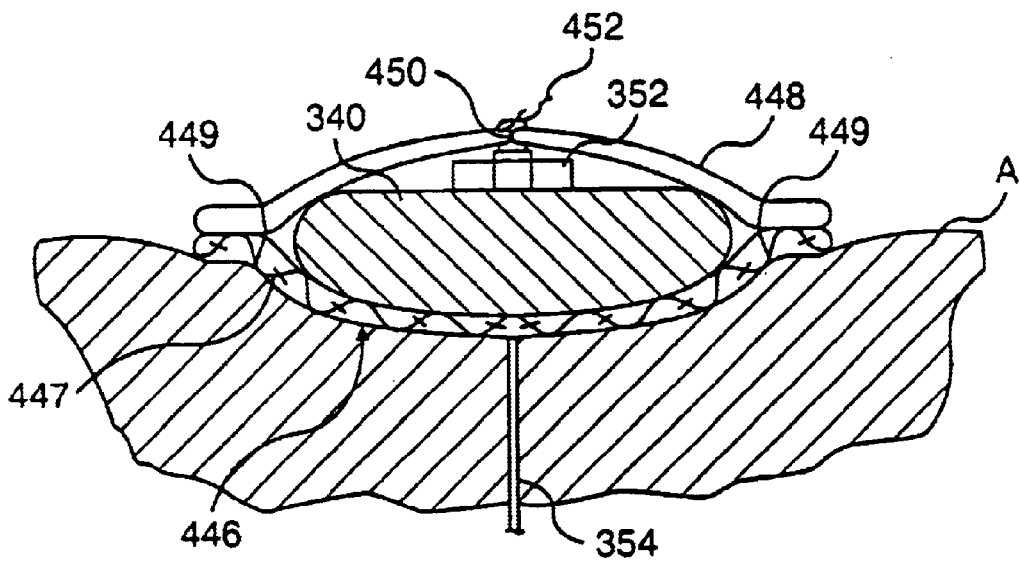
FIG. 30 is a cross sectional view of the pad including an envelope.

FIG. 30 illustrates yet another alternative approach to securing the anchors or anchor pads to the heart surface. FIG. 30 is a cross sectional view of an anchor pad 340 disposed on heart A. Anchor pad 340 is disposed within an envelope 446. Envelope 446 includes a bottom layer 447 disposed between anchor pad 340 and heart A and a top layer 448 disposed on the opposite side of anchor pad 340. Layers 347 and 340 are held together by sutures 449. Bottom layer 447 is preferably a mesh or expanded PTFE which has a pore size or intranodial dimension sufficient to promote tissue ingrowth. The pore size is preferably between about 10 and about 100 microns and more preferably, between about 20 and about 40 microns. With respect to expanded PTFE, the intranodial dimension is preferably between about 10 to about 100 microns and more preferably between about 2 to about 40 microns. The top material could also be expanded PTFE or the like having a pore size which preferably does not promote ingrowth and thus resists adhesion to surrounding tissue. As an alternative embodiment, the pores could be formed directly in the pad surface.

Figure 31:
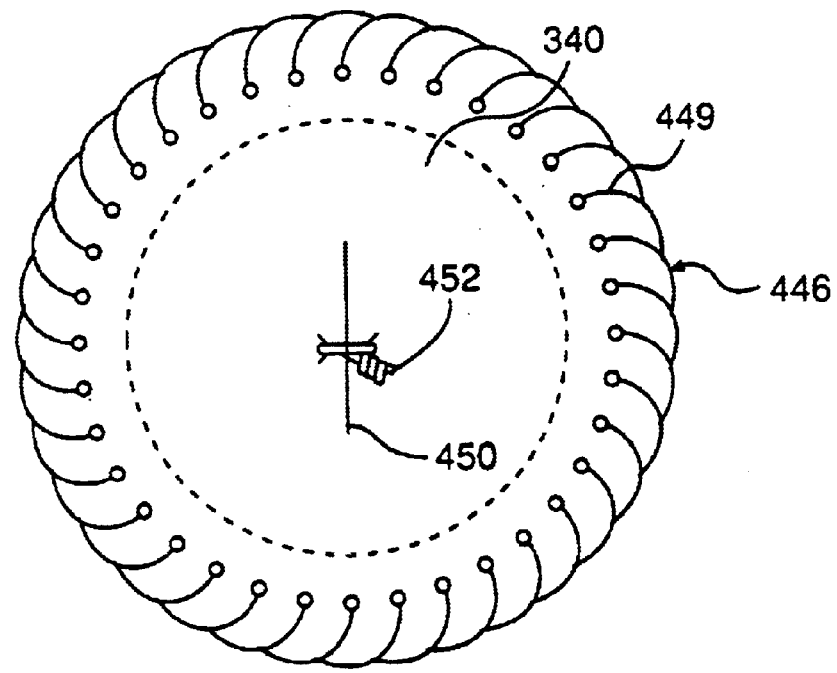
FIG. 31 shows the envelope of FIG. 30.

Envelope 446 would preferably be placed around pad 340 prior to placing pad 340 on tension member 354. A window 450 can be provided to provide access to nut 352 to secure pads to tension member 354. After tightening nut 352, window 450 can be closed by suture 452. FIG. 31 is a top view of pad 340 and envelope 446 of FIG. 30. It can be appreciated that a similar envelope can be placed around the various anchor pads disclosed herein. The location of the window may have to vary, however, to provide access to the respective means for securing the anchor pads to the tension member.

The splints of the present invention can be implanted acutely or chronically. When the splints are implanted chronically, it is particularly important that the tension member or members be highly fatigue resistant. Typical materials for the tension member can include, among other biocompatible materials, stainless steel, titanium alloys, NiTi alloys such as Nitinol or elgiloy. In a preferred embodiment, the tension member is a wire having a diameter of between 0.005 to 0.035 inches in diameter or, more preferably, between 0.01 and 0.02 inches in diameter and, most preferably, about 0.014 inches in diameter. The length of the tension member between the pads is preferably about 0.6 to 4 inches, and more preferably, between about 1 to 3 inches and, most preferably, about 2 inches. To improve the fatigue resistance of the metallic tension members, their surface can be electro-polished, buffed or shot peened. Drawing or arnealing of the metal will also improve fatigue resistance.

The tension member, in a preferred embodiment, articulates with respect to the anchor pad to reduce bending of the tension member at the pad. This can be accomplished by a ball and socket joint shown in FIG. 22, for example. The tension member itself can be made more flexible or bendable by providing a multi-filament tension member such as a braided or twisted wire cable tension member. A multifiber filament structure of numerous smaller wires can then easily, while reducing the stress level on any individual wire as compared to a solid wire of the same diameter as the multifilament bundle. Such a multi-filament tension member can be made from biocompatible materials such as, but not limited to, stainless steel, Nitinol, titanium alloys, LCP (liquid crystal polymer), Spectra™ fiber, kevlar fiber, or carbon fiber. In a preferred embodiment, the multi-filament structure is coated or covered to substantially seal the multi-filament structure. Coatings such as silicone, urethane or PTFE are preferred.

Figure 32:
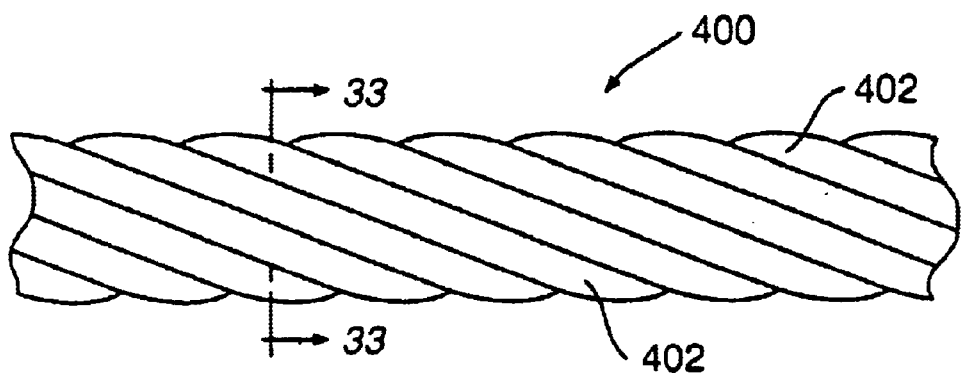
FIG. 32 is a side view of a multifilament twisted cable.
Figure 33:
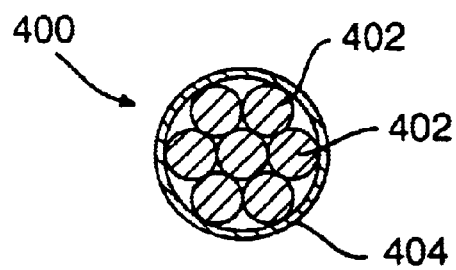
FIG. 33 is a cross sectional of the cable of FIG. 32.

FIG. 32 is a side view of multifilament twisted cable 400. Cable 400 includes a plurality of wires or filaments 402 twisted about the longitudinal axis of cable 400. FIG. 33 is a transverse cross sectional view of cable 400. In FIG. 33, cable 400 includes a surrounding coating 404 not shown in FIG. 32.

Figure 34:
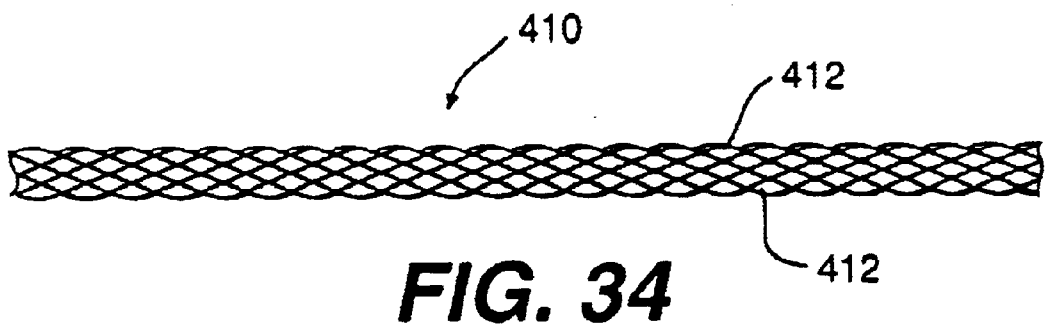
FIG. 34 is a side of a multifilament braided tension member.

FIG. 34 is a side view of a braided multifilament tension member 410. Tension member 410 includes a plurality of filaments or wires 412. It can be appreciated that numerous braiding patterns are known to those skilled in the art of multifilament members. It is anticipated that in a preferred embodiment, braided member 410 can have an optional core of fibers running parallel to an elongate axis of tension member 410. In yet another preferred embodiment, tension member 410 could have a solid wire core extending parallel to and along the longitudinal axis of tension member 410.

The tension members and anchors or anchor pads are preferably bio-resistant, i.e., resistant to physiologic attack. To improve bio-resistance, tension member and/or anchors or anchor pads can be coated with carbon material such as glass, pyrolytic carbon, diamond or graphite, zirconium nitrate or oxide. Roughened or porous urethanes, silicone or polymer coatings or sheaths can be used to promote tissue ingrowth to create a biological seal. Hydrophilic and albumin coatings can also be used. Drugs incorporated into a binder coating can also be used to reduce biological attack on the splint and irritation of tissue by the splint. Such drugs include heparin, coumadin, anti-inflammatory steroid or ASA-aspirin. The oxide layer of the underlying metal could also be optimized to improve bio-resistance. This is particularly true for stainless steel, titanium, or nickel titanium on which an oxide layer can be formed by heating the component to improve biocompatibility. Further coatings include calcium hydroxy appetite, beta tricalcium phosphate and aluminum oxide can be applied to the tension member. The tension member and/or pad or anchor pad can at least be, in part, formed from titanium to enhance electronegativity.

The anchors or anchor pads and, particularly the tension members are biocompatible, preferably antithrombogenic and made to prevent hemolysis. The coatings used to enhance bio-resistance described above can generally be used to improve biocompatibility. Since the tension member is exposed to significant blood flows through the left ventricle, in a preferred embodiment, the tension member has a generally small size and shape elliptical cross sectional shape to reduce turbulence or drag over the tension member. If such elliptical, transverse cross section tension member were used, it can be appreciated that the narrow end would be preferably oriented toward the direction of blood flow. It is also desirable to select a tension member material and shape which would not vibrate at resonant frequency under the influence of blood flow.

Where the tension member passes through the heart wall, various approaches can be taken to reduce or prevent bleeding. For example, the surface of the anchor or anchor pad and/or tension member in contact with the heart wall can be coated or include an ingrowth inducing covering such as collagen, dacron, expanded PTFE or a roughened/porous surface. A clotting inducing substance may also be bound to the tension member and/or anchor or anchor pads, such as avitene or collagen. It is also contemplated that the portion of the heart wall where the tension member passes through could be cauterized. In a preferred embodiment, the tissue can be cauterized by heating the tension member. A glue such as cyanoacrylate can also be disposed between the tension member and the heart wall to reduce or prevent bleeding from the heart wall. Mechanical means such as an O-ring or compression fitting could also be disposed between the heart wall and the tension member to reduce bleeding. A purse string suture can be placed on the heart, around the tension member adjacent the pad as well.

The tension member is preferably flexible enough to allow for changing interface conditions between the heart and the splint, and alternating pad orientation throughout the cardiac cycle. The flexibility should be sufficient enough to avoid injury to the heart or bleeding. It is also preferable that if the heart were to contract sufficiently enough to put the tension member in compression that it would readily buckle. Buckling could be promoted by providing a ribbon shaped tension member, chain link tension member, thin wire tension member, bent tension member or multi-filament tension.

The tension member is preferably radiopaque, echo cardiographic compatible, or MRI compatible or includes a marker which is radiopaque, echo compatible, or MRI compatible. The preferred locations for markers would include the center of the tension member and at the ends of the tension member disposed at the heart walls. The radiopaque markers could be gold or platinum or other biocompatible metal or heavy metal filled polymeric sleeves. With respect to echo compatible or MRI compatible tension members or markers, the tension or marker are preferably non-interfering or visible. Having radiopaque echo compatible or MRI compatible tension members or markers is particularly desirable for follow-up, non-invasive monitoring of the tension member after implantation. The presence of the tension member can be visualized and the distance between two or more markers measured. Integrity of the tension member can be confirmed as well.

In a preferred embodiment, the tension member is not conductive to the action potential of muscle. This can be accomplished by insulating the tension member, anchor and/or anchor pad interface or fabricating the tension member anchor and/or anchor pad from a non-conductive metal such as titanium.

In addition to monitoring the performance of the tension member by visualization techniques such as fluoroscopy or echo imagery, sensors can advantageously be incorporated into the splints. For example, a strain gauge can be disposed on a tension member to monitor the loading on the member in use. Strain can be related to load as known to those skilled in the art by developing a stress/strain relationship for a given tension member. The strain gauge can be connected by a biocompatible lead to a conventional monitoring device. A pressure gauge formed from, for example, piezo electric material can also be disposed on the tension member to monitor filling pressures or muscle contractility.

In a preferred embodiment, a tension member can be slidably enclosed within a tube. If the tension member were to fail, the tube would contain the tension member therein.

It is anticipated that the tension member could be connected to a pacing lead. In such an instance, if the tension member were conductive, pacing signals could be conveyed along the tension member from one heart wall to another.

In use, the various embodiments of the present invention are placed in or adjacent the human heart to reduce the radius or cross-section area of at least one chamber of the heart. This is done to reduce wall stress or tension in the heart or chamber wall to slow, stop or reverse failure of the heart. In the case of the splint 16 shown in FIG. 1, a cannula can be used to pierce both walls of the heart and one end of the splint can be advanced through the cannula from one side of the heart to the opposite side where an anchor can be affixed or deployed. Likewise, an anchor is affixed or deployed at the opposite end of splint 16. Additional methods for splint placement are described in more detail in U.S. application Ser. No. 09/123,977, filed on Jul. 29, 1998 and entitled "Transventricular Implant Tools and Devices" and incorporated herein by reference.

It can be appreciated that the methods described above to advance the tension members through the ventricles can be repeated to advance the desired number of tension members through the ventricle for a particular configuration. The length of the tension members can be determined based upon the size and condition of the patient's heart. It should also be noted that although the left ventricle has been referred to here for illustrative purposes, that the apparatus and methods of this invention can also be used to splint multiple chambers of a patient's heart as well as the right ventricle or either atrium.

Figure 35:
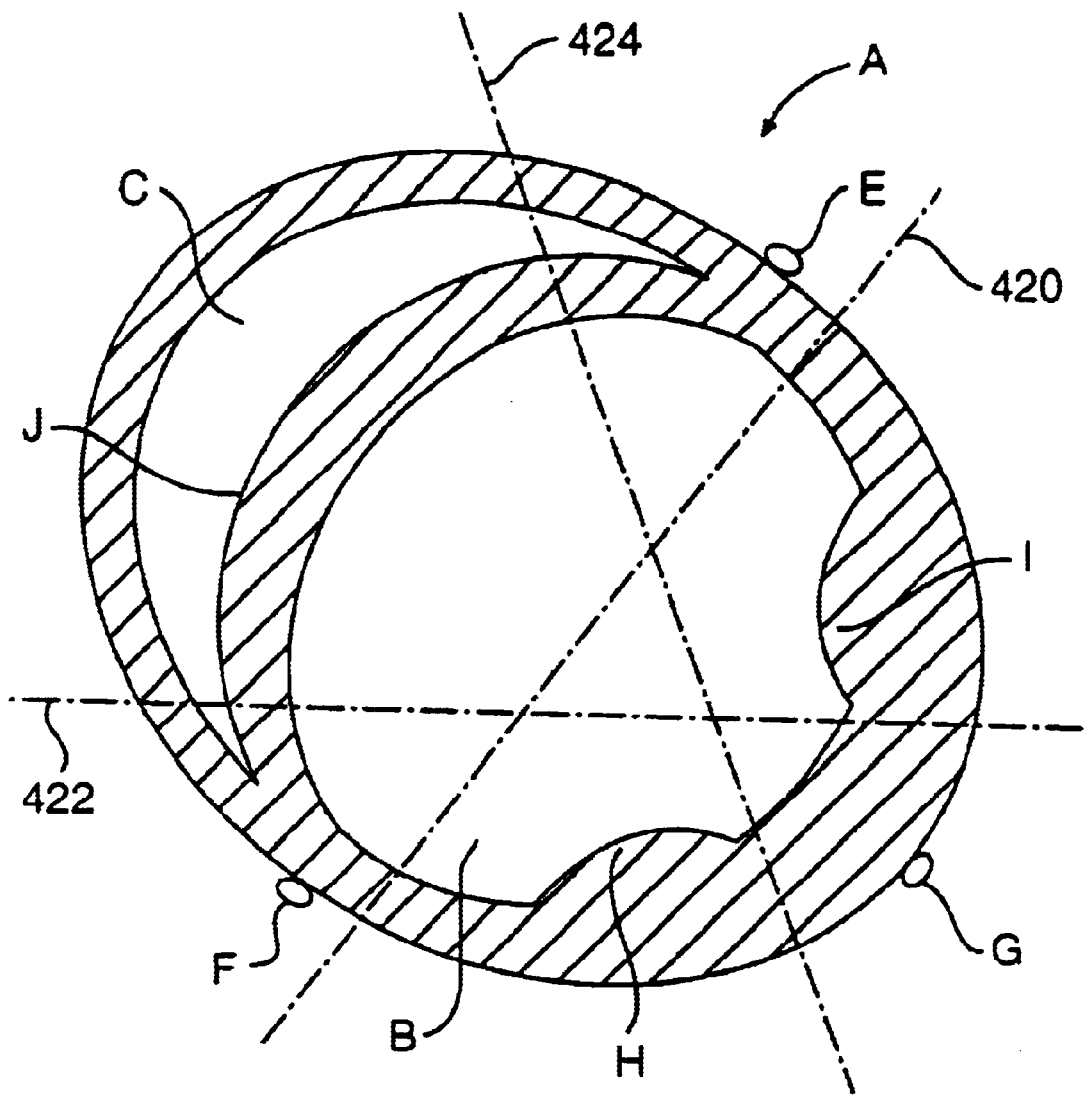
FIG. 35 is a schematic generally horizontal cross sectional view of the heart showing preferred tension member alignments.

FIG. 35 is a schematic view of generally horizontal cross section of heart A including left ventricle B and right ventricle C. Also shown are left anterior descending artery E, posterior descending artery F, obtuse marginal artery G, postero-medial papillary muscle H and antero-lateral papillary muscle I. Shown in FIG. 35 are three generally horizontal preferred alignments for tension member placement for the splints of the present invention. These alignments generally met three goals of splint positioning including good bisection of the left ventricle, avoidance of major coronary vessels and avoidance of valve apparatus including chordae leaflets and papillary muscles. Alignment 420 can be referred to as the anterior/posterior (AP) position. Alignment 422 can be referred as the posterior septal/lateral wall (PSL) position. Alignment 424 can be referred to as the anterior septal/lateral wall (ASL) position.

It can be appreciated that the alignments shown illustrative only and that the alignments may be shifted or rotated about a vertical axis generally disposed through the left ventricle and still avoid the major coronary vessels and papillary muscles. When the alignment passes through a substantial portion of right ventricle C, it may be desirable to dispose not only two pads on the exterior of the heart at opposite ends of a tension member, but also a third pad within right ventricle C on septum J. The spacing between the third pad and the pad disposed outside the heart proximate left ventricle B preferably defines the shape change of left ventricle B. This will allow the spacing of the third pad relative to the pad disposed outside the heart proximate right ventricle C to define a shape change if any of right ventricle C in view of the spacing between those pads. With the alignments as shown in FIG. 35, the third pad will be unnecessary. It is likely, however, that with alignments 422 and 424 in order to achieve the desired shape change of left ventricle B, the exterior pad of the wall proximate the right ventricle C will be drawn into contact with septum J. This will consequently somewhat reduce the volume of right ventricle C.

Figure 36:
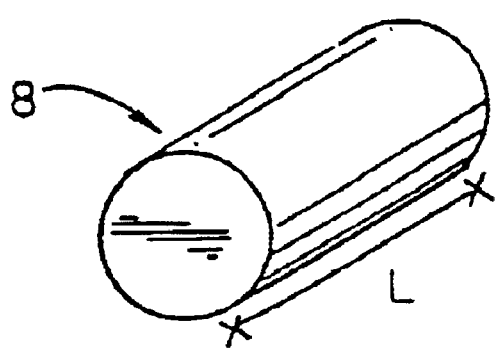
FIG. 36 is a idealized cylindrical model of a left ventricle of a human heart.

FIG. 36 is a view of a cylinder or idealized heart chamber 48 which is used to illustrate the reduction of wall stress in a heart chamber as a result of deployment of the splint in accordance with the present invention. The model used herein and the calculations related to this model are intended merely to illustrate the mechanism by which wall stress is reduced in the heart chamber. No effort is made herein to quantify the actual reduction which would be realized in any particular in vivo application.

Figure 37:
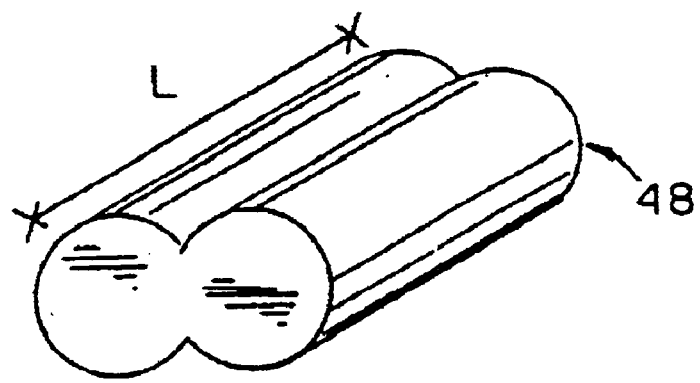
FIG. 37 is a splinted model of the left ventricle of FIG. 14.

FIG. 37 is a view of the idealized heart chamber 48 of FIG. 36 wherein the chamber has been splinted along its length L such that a "figure eight" cross-section has been formed along the length thereof. It should be noted that the perimeter of the circular transverse cross-section of the chamber in FIG. 36 is equal to the perimeter of the figure eight transverse cross-section of FIG. 37. For purposes of this model, opposite lobes of the figure in cross-section are assumed to be mirror images.

Figure 38:
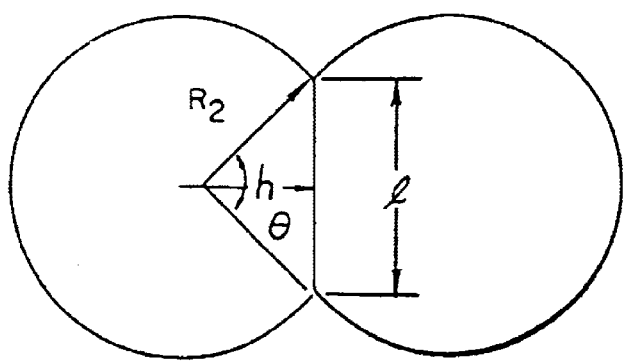
FIG. 38 is a transverse cross-sectional view of FIG. 15 showing various modeling parameters.

FIG. 38 shows various parameters of the FIG. 1 cross-section of the splinted idealized heart chamber of FIG. 37. Where l is the length of the splint between opposite walls of the chamber, $R_2$ is the radius of each lobe, $\theta$ is the angle between the two radii of one lobe which extends to opposite ends of the portion of the splint within chamber 48 and h is the height of the triangle formed by the two radii and the portion of the splint within the chamber 48 ($R_1$ is the radius of the cylinder of FIG. 36). These various parameters are related as follows:

$$h = R_2 \cos(\theta/2)$$

$$l = 2R_2 \sin(\theta/2)$$

$$R_2 = R_1 \pi/(2\pi - \theta)$$

From these relationships, the area of the figure eight cross-section can be calculated by:

$$A_2 = 2\pi(R_2)^2(1 - \theta/2\pi) + hl$$

Where chamber 48 is unsplinted as shown in FIG. 36 $A_1$, the original cross-sectional area of the cylinder is equal to $A_2$ where $\theta = 180°$, $h = 0$ and $l = 2R_2$. Volume equals $A_2$ times length L and circumferential wall tension equals pressure within the chamber times $R_2$ times the length L of the chamber.

Thus, for example, with an original cylindrical radius of four centimeters and a pressure within the chamber of 140 mm of mercury, the wall tension T in the walls of the cylinder is 104.4 newtons. When a 3.84 cm splint is placed as shown in FIGS. 37 and 38 such that l=3.84 cm, the wall tension T is 77.33 newtons.

Figure 39:
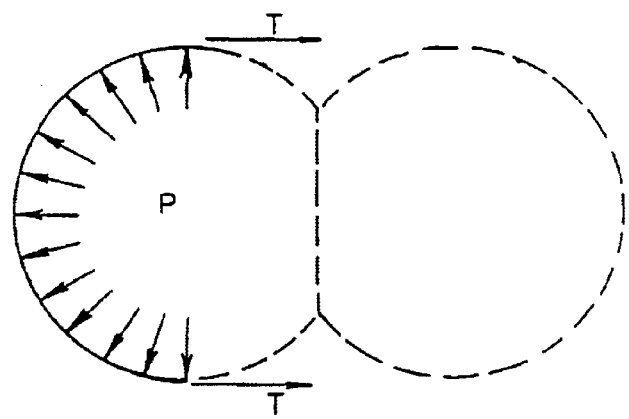
FIG. 39 is a transverse cross-section of the splinted left ventricle of FIG. 15 showing a hypothetical force distribution.
Figure 40:
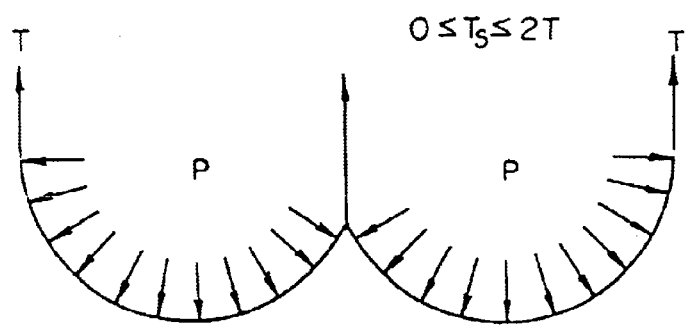
FIG. 40 is a second transverse cross-sectional view of the model left ventricle of FIG. 15 showing a hypothetical force distribution.

FIGS. 39 and 40 show a hypothetical distribution of wall tension T and pressure P for the figure eight cross-section. As θ goes from 180° to 0°, tension $T_5$, in the splint goes from 0 to a 2T load where the chamber walls carry a T load.

In yet another example, assuming that the chamber length L is a constant 10 cm, the original radius $R_1$ is 4 cm, at a 140 mmHg the tension in the walls is 74.7 N. If a 4.5 cm splint is placed such that l=4.5 cm, the wall tension will then be 52.8 N.

When a splint is actually placed on the heart, along an alignment such as those shown in FIG. 35, the length 1 between the two pads as measured along the tension member is preferably 0.4 to about 0.8 and more preferably between about 0.5 to about 0.7 and most preferably about 0.6 times the distance along the length of the tension member at end diastole if the pads were not secured to the tension member and provided no resistance to expansion of the heart. A more detailed discussion of tension member length can be found in U.S. application Ser. No. 09/123,977, filed on Jul. 29, 1998 and entitled "Transventricular Implant Tools and Devices" which is incorporated herein by reference.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A method of placing an elongate member transverse a left ventricle of a heart the method comprising:
    placing the elongate member transverse the left ventricle so that a first end of the elongate member extends through a first wall of the left ventricle adjacent a papillary muscle in the left ventricle, and a second end of the elongate member extends through a second heart wall; and
    attaching an anchoring device to the elongate member external the heart to maintain a position of the elongate member transverse the left ventricle.

2. The method of claim 1, wherein the first end of the elongate member extends through the first wall between a left anterior descending artery and a postero-medial papillary muscle.

3. The method of claim 2, wherein the second heart wall is a wall of a right, ventricle.

4. The method of claim 3, wherein the elongate member extends through a septal wall of the heart.

5. The method of claim 2, wherein the second heart wall is a wall of a right ventricle adjacent a posterior descending artery.

6. The method of claim 1, wherein the first end of the elongate member extends through the first wall adjacent an antero-lateral papillary muscle and closer to an antero-lateral papillary muscle than to a postero-medial papillary muscle.

7. The method of claim 6, wherein the second heart wall is a wall of a right ventricle.

8. The method of claim 7, wherein the second heart wall is a wall of a right ventricle proximate a posterior descending artery.

9. The method of claim 7, wherein the elongate member extends through a septal wall of the heart.

10. The method of claim 1, wherein the first end of the elongate member extends through the first wall between a left anterior descending artery and an obtuse marginal artery.

11. The method of claim 10, wherein the second heart wall is a wall of a right ventricle.

12. The method of claim 11, wherein the second heart wall is a wall of a right ventricle adjacent a posterior descending artery.

13. The method of claim 11, wherein the elongate member extends through a septal wall of the heart.

14. The method of claim 1, wherein the first end of the elongate member extends through the first wall between a left anterior descending artery and an antero-lateral papillary muscle.

15. The method of claim 14, wherein the second heart wall is a wall of the heart adjacent a posterior descending artery.

16. The method of claim 1, wherein the elongate member extends through a septal wall of the heart.

17. The method of claim 1, wherein the second heart wall is a wall of a right ventricle of the heart.

18. The method of claim 1, wherein attaching the anchoring device to the elongate member includes placing a first anchoring member and a second anchoring member external the heart, the first and second anchoring members being attached respectively to the first and second ends of the elongate member.

19. A method of placing a device on a heart, comprising:
    placing the device in a position on a left ventricle so that the device contacts a first wall of the left ventricle between a left anterior descending artery and a papillary muscle and so that the device contacts a second heart wall opposite the first wall; and
    anchoring the device external the heart to maintain the position of the device on the left ventricle.

20. The method of claim 19, wherein the device includes an elongate member, and further comprising placing the elongate member transverse the left ventricle.

21. The method of claim 20, wherein anchoring the device includes attaching an anchoring device to the elongate member.

22. The method of claim 20, wherein a first end of the elongate member extends through the first wall between the left anterior descending artery and a postero-medial papillary muscle.

* * * * *

UNITED STATES PATENT AND TRADEMARK OFFICE
CERTIFICATE OF CORRECTION

PATENT NO. : 6,629,921 B1 Page 1 of 1
DATED : October 7, 2003
INVENTOR(S) : Cyril J. Schweich, Jr. et al.

It is certified that error appears in the above-identified patent and that said Letters Patent is hereby corrected as shown below:

Title page,
Item [63], insert -- which is a continuation of application No. 09/124,286, filed on Jul. 29, 1998, now Pat. No. 6,045,497, -- before "which is a continuation-in-part"; Delete ", which is a continuation of application No. 09/124,286, filed on Jul. 29, 1998, now Pat. No. 6,045,497";

Column 15,
Line 28, replace "heart the" with -- heart, the --; and
Line 43, replace "right, ventricle." with -- right ventricle. --.

Signed and Sealed this

Twenty-third Day of March, 2004

JON W. DUDAS
*Acting Director of the United States Patent and Trademark Office*